United States Patent
Lai

(10) Patent No.: US 9,060,896 B2
(45) Date of Patent: Jun. 23, 2015

(54) EARWAX CLEANER

(71) Applicant: Shyh-Jen Lai, New Taipei (TW)

(72) Inventor: Shyh-Jen Lai, New Taipei (TW)

(*) Notice: Subject to any disclaimer, the term of this patent is extended or adjusted under 35 U.S.C. 154(b) by 253 days.

(21) Appl. No.: 13/909,271

(22) Filed: Jun. 4, 2013

(65) Prior Publication Data

US 2014/0052163 A1    Feb. 20, 2014

(30) Foreign Application Priority Data

Aug. 20, 2012 (TW) .................................. 101215945

(51) Int. Cl.
  *A61F 9/00*   (2006.01)
  *A61F 11/00*  (2006.01)
  *A61M 1/00*   (2006.01)

(52) U.S. Cl.
  CPC ............ *A61F 11/006* (2013.01); *A61M 1/0023* (2013.01)

(58) Field of Classification Search
  CPC . A61F 11/006; A61M 1/0023; A61M 3/0262; A61M 3/0279; A61M 3/0283; A61M 3/0291; A61B 10/0283; A61B 10/02; A61B 2010/0216; A61B 10/0291
  See application file for complete search history.

(56) References Cited

U.S. PATENT DOCUMENTS

| | | | | |
|---|---|---|---|---|
| 4,167,186 A | * | 9/1979 | Pick et al. | 604/212 |
| 4,405,321 A | * | 9/1983 | Budoff | 604/212 |
| 4,519,794 A | * | 5/1985 | Sneider | 604/212 |
| 5,421,818 A | * | 6/1995 | Arenberg | 604/21 |
| 5,632,756 A | * | 5/1997 | Kruglick | 606/162 |
| 5,895,408 A | * | 4/1999 | Pagan | 606/199 |
| 5,921,998 A | * | 7/1999 | Tano et al. | 606/161 |
| 8,945,142 B2 | * | 2/2015 | Schaeffer et al. | 606/108 |
| 2003/0181933 A1 | * | 9/2003 | Eicoff | 606/162 |
| 2006/0156501 A1 | * | 7/2006 | Grunberger | 15/209.1 |
| 2006/0287656 A1 | * | 12/2006 | Brown et al. | 606/127 |
| 2007/0135773 A1 | * | 6/2007 | Yoo | 604/275 |
| 2009/0112241 A1 | * | 4/2009 | Bar et al. | 606/162 |
| 2010/0211021 A1 | * | 8/2010 | Wong | 604/247 |
| 2010/0312198 A1 | * | 12/2010 | Guidi | 604/257 |
| 2011/0066172 A1 | * | 3/2011 | Silverstein | 606/162 |
| 2011/0282368 A1 | * | 11/2011 | Swayze et al. | 606/159 |
| 2013/0184684 A1 | * | 7/2013 | Yardley | 604/514 |

* cited by examiner

*Primary Examiner* — Jonathan W Miles
(74) *Attorney, Agent, or Firm* — Jackson IPG PLLC; Demian K. Jackson

(57) ABSTRACT

An earwax cleaner includes a bag-shaped holding portion and a soft earwax picking sleeve. The rear section of the bag-shaped holding portion is provided with a resilient bag-shaped body, and the front section is a pipe with an opening. The earwax picking sleeve has a reduced mouth at the distal end and a plurality of protrusions on an outer wall thereof. The earwax picking sleeve is fitted on the pipe of the holding portion. The opening of the pipe is aligned with the mouth of the earwax picking sleeve to form an open end for the air in the bag-shaped body of the holding portion to pass in and out. When in use, the pipe is inserted in the ear and the holding portion is slightly turned with the protrusions to pick the earwax from the wall of the ear to be collected in the bag-shaped body.

4 Claims, 4 Drawing Sheets

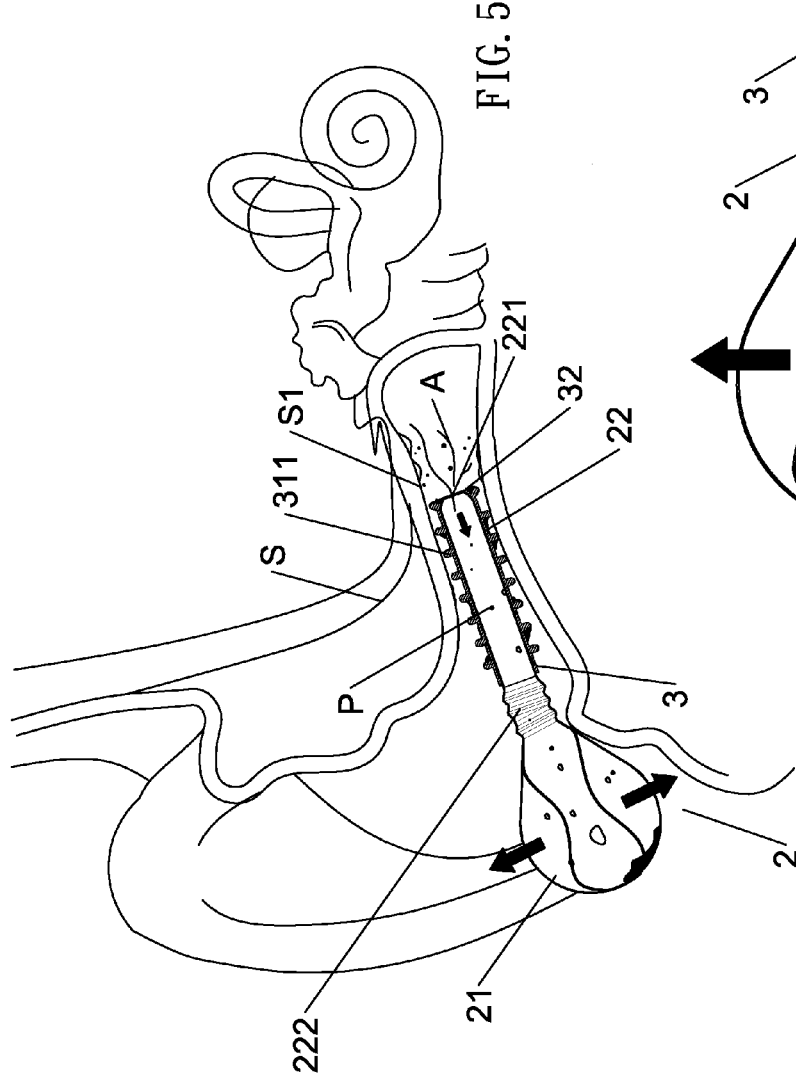
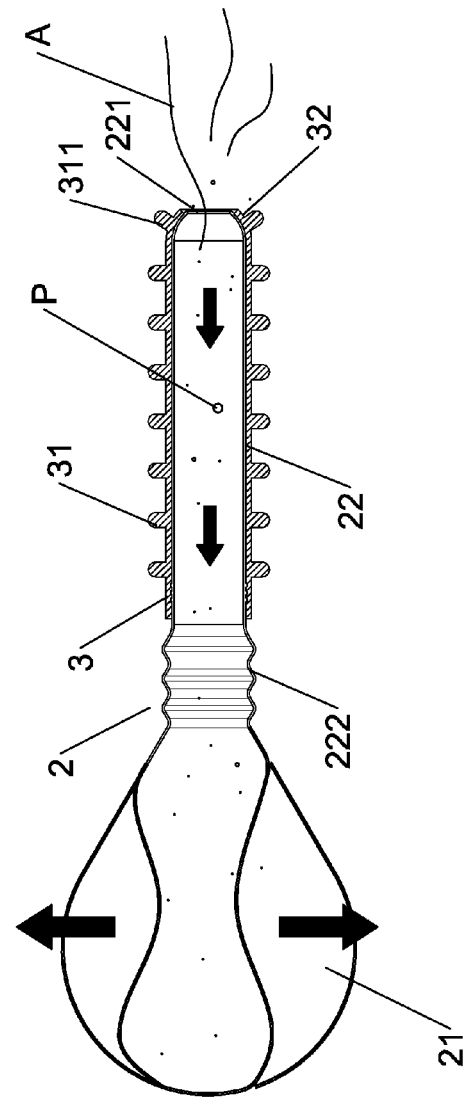
FIG. 5
FIG. 5A

EARWAX CLEANER

BACKGROUND OF THE INVENTION

1. Field of the Invention

The present invention relates to an earwax cleaner, and more particularly to an earwax cleaner which has a suction configuration and protrusions on a front section thereof to pick earwax from the wall of the ear. The earwax can be removed and collected in a bag-shaped body.

2. Description of the Prior Art

There are various earwax picks on the market. In general, the earwax pick has a soft protruding bit at the front end thereof to pick earwax. Sometimes, the earwax pick may hurt the ear. In addition, it is necessary to use a clip or a brush to clip and remove the earwax. The clip/brush may harm the ear by accident.

A professional earwax cleaner, like a vacuum cleaner, has a suction nozzle. The suction nozzle is inserted in the ear to vacuum the earwax. This cleaning action is better and safe. However, during operation, there is a noise in high decibel. The user feels uncomfortable. Particularly, the professional earwax cleaner is expensive and occupies a lot of space. A household or an individual is unable to have the equipment or to operate by himself/herself.

Some people use an earwax pick and a snot cleaner to remove earwax. However, it is inconvenient to prepare for both tools.

Accordingly, the inventor of the present invention has devoted himself based on his many years of practical experiences to solve these problems.

SUMMARY OF THE INVENTION

The primary object of the present invention is to provide an earwax cleaner which is able to expel earwax. The earwax cleaner comprises a bag-shaped holding portion and a soft earwax picking sleeve. The rear section of the bag-shaped holding portion is provided with a resilient bag-shaped body, and the front section is a pipe with an opening. The earwax picking sleeve is fitted on the pipe of the holding portion. The earwax is convenient to take along and to operate.

A further object of the present invention is to provide an earwax cleaner which comprises a soft earwax picking sleeve having a protrusions thereon. The earwax picking sleeve is inserted in the ear and slightly turned with the protrusions to pick earwax from the wall of the ear. The bag-shaped body is pressed and then released to suck the earwax into the bag-shaped body. The earwax can be removed simply, preventing the ear from being damaged.

A further object of the present invention is to provide an earwax cleaner which comprises a soft earwax picking sleeve fitted on the front section of the bag-shaped holding portion. The earwax picking sleeve can be replaced on a regular time schedule, prevent it from being infected.

BRIEF DESCRIPTION OF THE DRAWINGS

FIG. 3-A is a partial enlarged sectional view of the present invention;
FIG. 4-A is a schematic view of FIG. 4;
FIG. 5 is a second schematic view of the present invention wen in use;
and
FIG. 5-A is a schematic view of FIG. 5.

DETAILED DESCRIPTION OF THE PREFERRED EMBODIMENTS

Embodiments of the present invention will now be described, by way of example only, with reference to the accompanying drawings.

Figure 1:
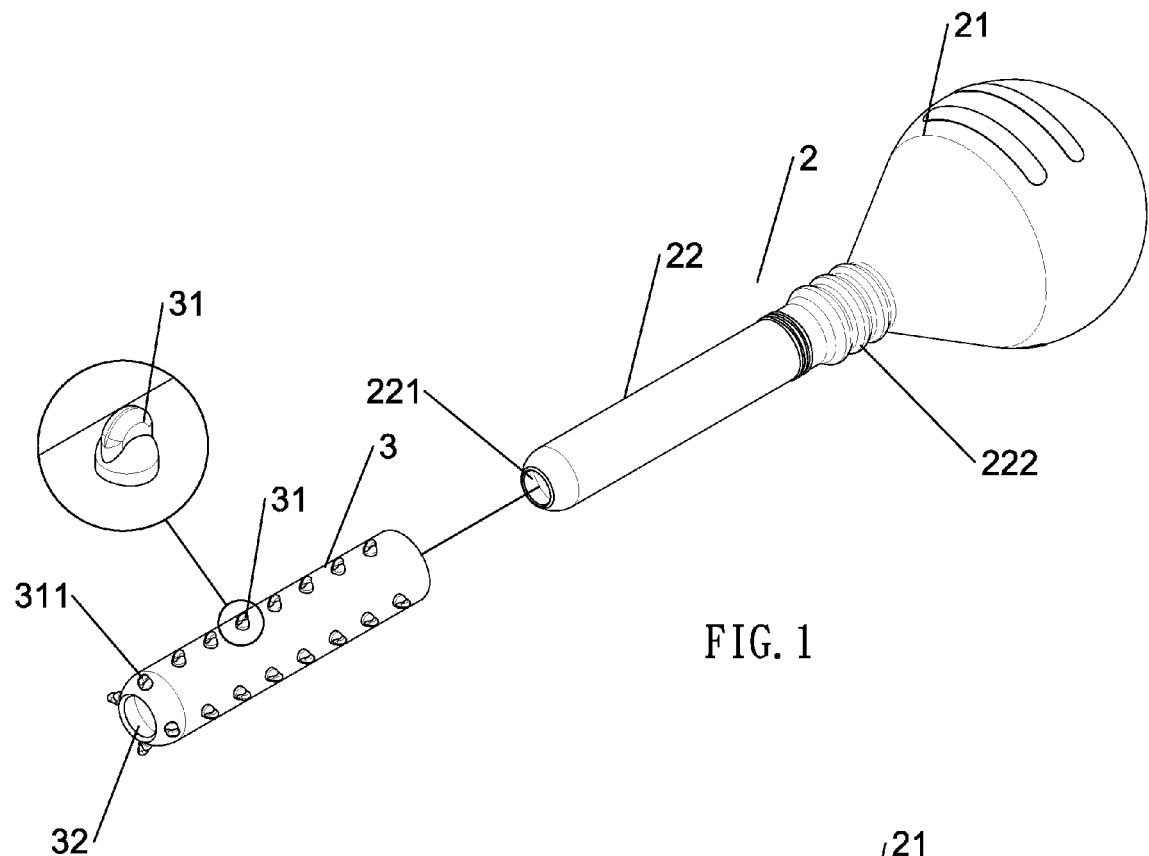
FIG. 1 is an exploded view of the present invention.
Figure 2:
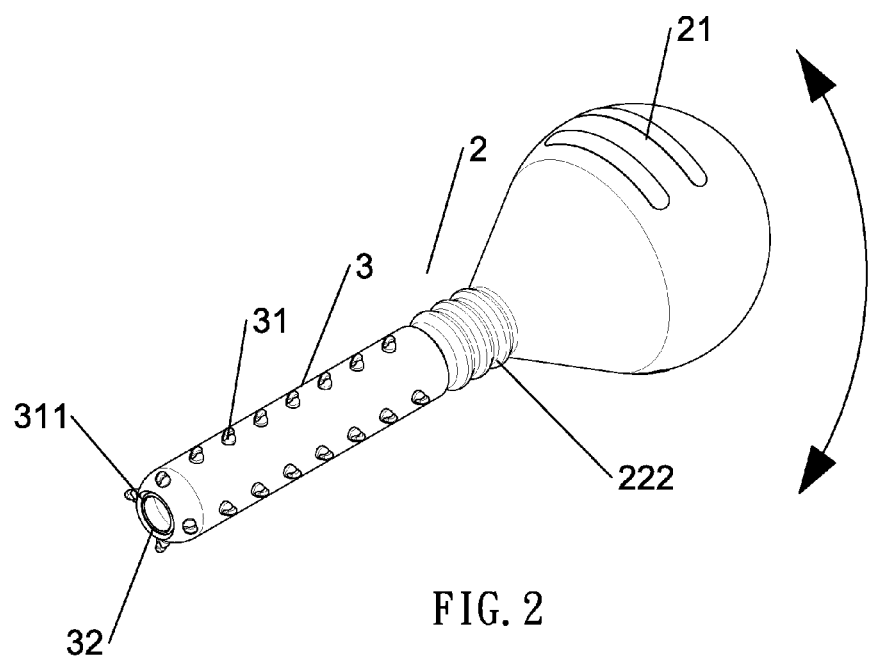
FIG. 2 is a perspective view of the present invention.
Figure 3A:
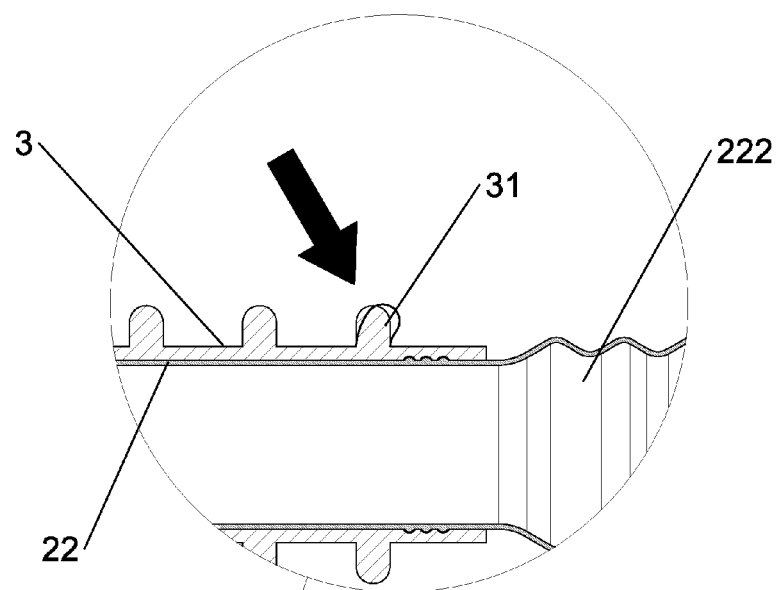
FIG. 3 is a sectional view of the present invention.
Figure 3:
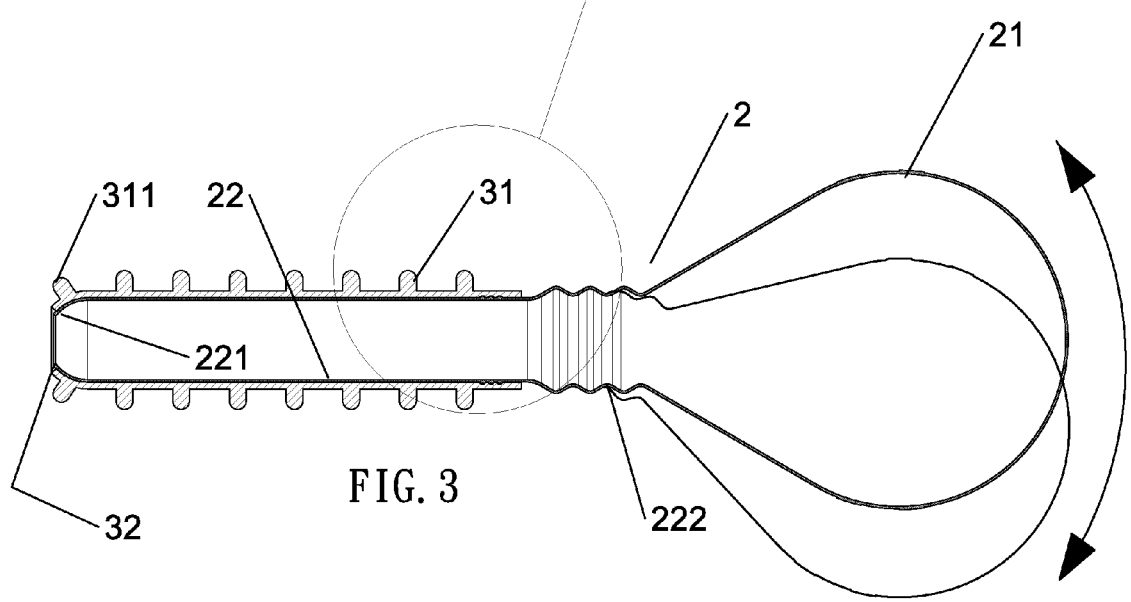

As shown in FIG. 1, FIG. 2, FIG. 3 and FIG. 3-A, the earwax cleaner of the present invention comprises a bag-shaped holding portion 2 and a soft earwax picking sleeve 3.

The rear section of the holding portion 2 is hollow and provided with a resilient bag-shaped body 21. The bag-shaped body 21 is able to inhale and exhale the air A when pressed and released. The front section of the holding portion 2 is a pipe 22 with an opening 221.

The earwax picking sleeve 3 is made of a soft material, such as silicone, rubber or silicone rubber. The earwax picking sleeve 3 has a reduced mouth 32 at a distal end thereof and a plurality of protrusions 31 on an outer wall thereof. The protrusions 31 are spaced and arranged in different directions. The earwax picking sleeve 3 is fitted on the pipe 22 of the holding portion 2. The opening 221 of the pipe 22 is aligned with the mouth 32 of the earwax picking sleeve 3 to form an open end for the air in the bag-shaped body 21 of the holding portion 2 to pass in and out.

Figure 4:
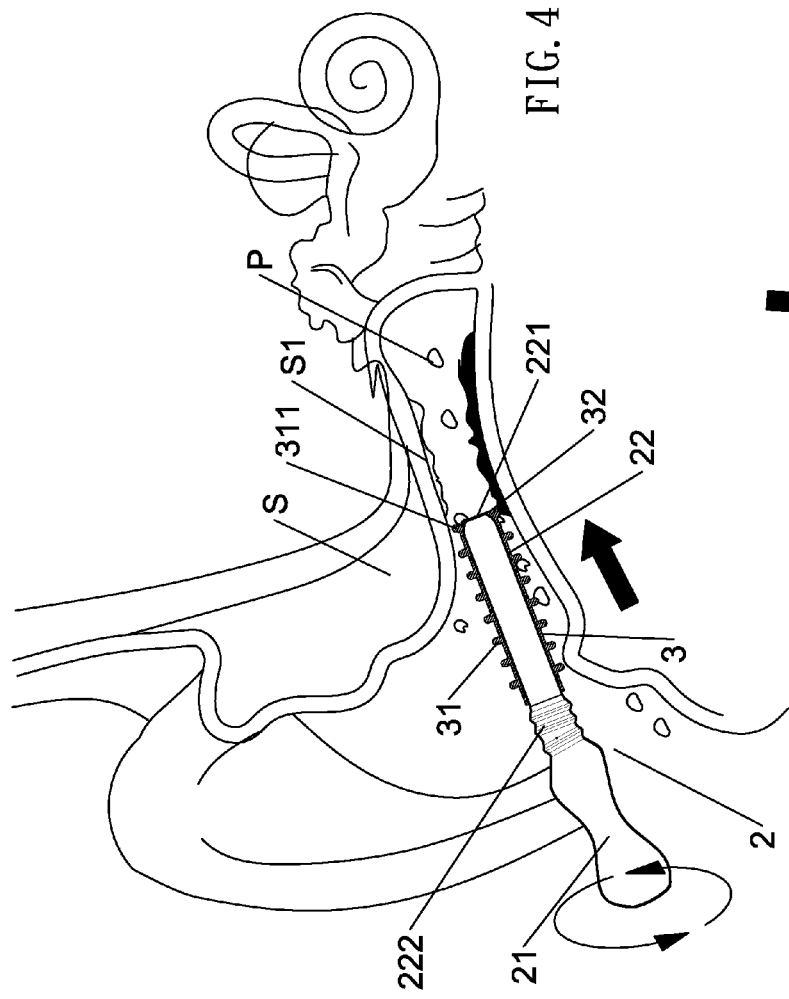
FIG. 4 is a first schematic view of the present invention wen in use.
Figure 4A:
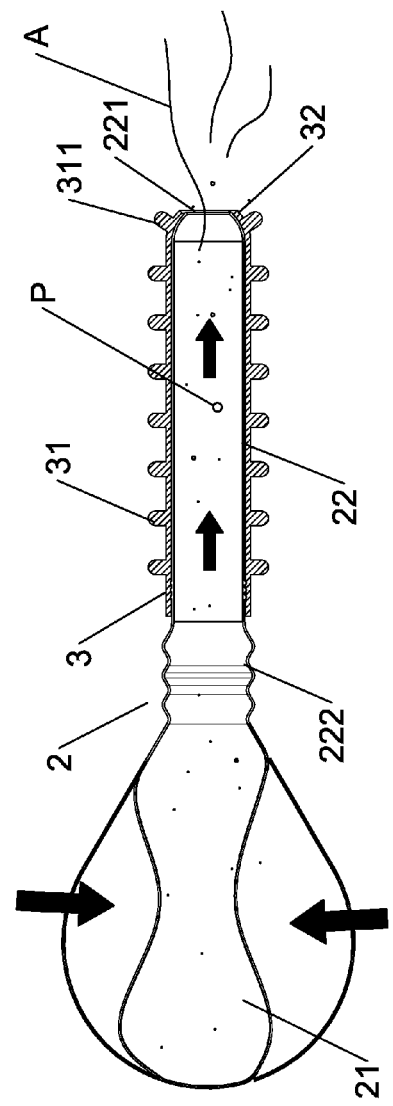

As shown in FIG. 4-A, the user holds and presses the holding portion 2 with his/her fingers so the bag-shaped body 21 is compressed flat to expel the inside air A. The pipe 22 is inserted in the ear S and the holding portion 2 is slightly turned, such that the protrusions 31 of the earwax picking sleeve 3 fitted on the pipe 2 pick the earwax P from the wall S1 of the ear S and then the earwax P falls in the ear S.

As shown in FIG. 5 and FIG. 5-A, when the holding portion 2 is released, the bag-shaped body 21 will restore to its original shape. The opening 221 at the front end of the pipe 22 inhales the surrounding air A, and then the surrounding earwax P is sucked and collected in the bag-shaped body 21.

After the entire ear cleaner is removed from the ear S, the user presses and releases the bag-shaped body 21 repeatedly to expel the earwax P from the bag-shaped body 21.

The bag-shaped body 21 is pressed and released and the pipe 22 is inserted in the ear S repeatedly in order to clean the earwax P thorough.

As shown in the drawings, the pipe 22 further has a wavy portion 222 at a rear end thereof, so that the user can bend the pipe 22 slightly to adjust the angle to pick the earwax conveniently.

As shown in the drawings, the earwax picking sleeve 3 has inclined protrusions 311 at a front end thereof. The inclined protrusions 311 are inclined forward and disposed close to the mouth 32 for providing a better effect to pick the earwax.

Although particular embodiments of the present invention have been described in detail for purposes of illustration, various modifications and enhancements may be made without departing from the spirit and scope of the present invention. Accordingly, the present invention is not to be limited except as by the appended claims.

What is claimed is:

1. An earwax cleaner, comprising:
a bag-shaped holding portion, a rear section of the holding portion being hollow and provided with a resilient bag-shaped body, the bag-shaped body being able to inhale and exhale air when pressed and released, a front section of the holding portion being a pipe with an opening; and a soft earwax picking sleeve, the earwax picking sleeve having a reduced mouth at a distal end thereof and a plurality of protrusions on an outer wall thereof, the protrusions being spaced and arranged in different directions, the earwax picking sleeve being fitted on the pipe of the holding portion, the opening of the pipe being aligned with the mouth of the earwax picking sleeve to form an open end for the air in the bag-shaped body of the holding portion to pass in and out, wherein the pipe extends along the majority of a length of the earwax picking sleeve.

2. The earwax cleaner as claimed in claim 1, wherein the pipe further has a wavy portion at a rear end thereof.

3. The earwax cleaner as claimed in claim 1, wherein the earwax picking sleeve has inclined protrusions at a front end thereof, and the inclined protrusions are inclined forward and disposed close to the mouth.

4. The earwax cleaner as claimed in claim 1, wherein the earwax picking sleeve is made of silicone, rubber or silicone rubber.

\* \* \* \* \*